United States Patent [19]
Gentile

[11] 4,185,624
[45] Jan. 29, 1980

[54] DEVICE FOR EXTERNALLY EXERTING A HOLDING ACTION ON BONE TISSUES

[76] Inventor: Giulio Gentile, Via S. Martino ai Monti 8, Rome, Italy

[21] Appl. No.: 801,305

[22] Filed: May 27, 1977

[30] Foreign Application Priority Data

May 31, 1976 [IT] Italy .............................. 49736 A/76
Mar. 28, 1977 [IT] Italy .............................. 48715 A/77

[51] Int. Cl.² .................... A61F 5/04; A61B 17/18
[52] U.S. Cl. ............................ 128/92 A; 128/92 B
[58] Field of Search ............... 128/92 A, 92 R, 92 B, 128/84 R, 92 BA, 92 BB, 92 D

[56] References Cited

U.S. PATENT DOCUMENTS 1,997,466  4/1935  Longfellow ..................... 128/92 A

FOREIGN PATENT DOCUMENTS 1161507  3/1958  France ..................... 128/92 B
1206411  8/1959  France ..................... 128/92 A
2274266  1/1976  France ..................... 128/92 A
580406  8/1958  Italy ........................ 128/92 A

*Primary Examiner*—Ronald L. Frinks
*Attorney, Agent, or Firm*—Schwartz, Jeffery, Schwaab, Mack, Blumenthal & Koch

[57] ABSTRACT

Nail members penetrate a bone near a fracture and adjustable clamps secure the nails to the bone. The nails also adjustably clamped in a holding assembly laterally spaced from the bone to insure maintaining the nails in secure and fixed relation to each other.

12 Claims, 4 Drawing Figures

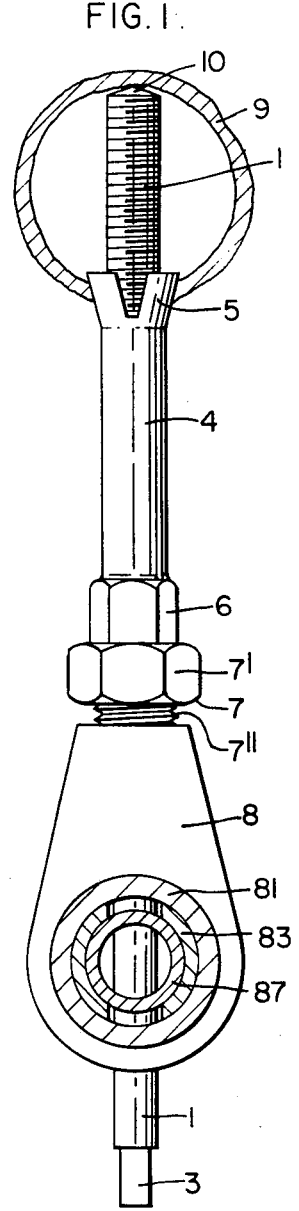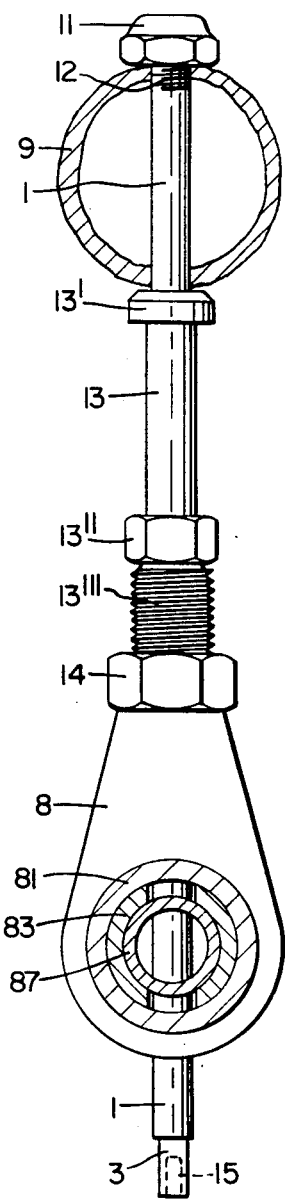

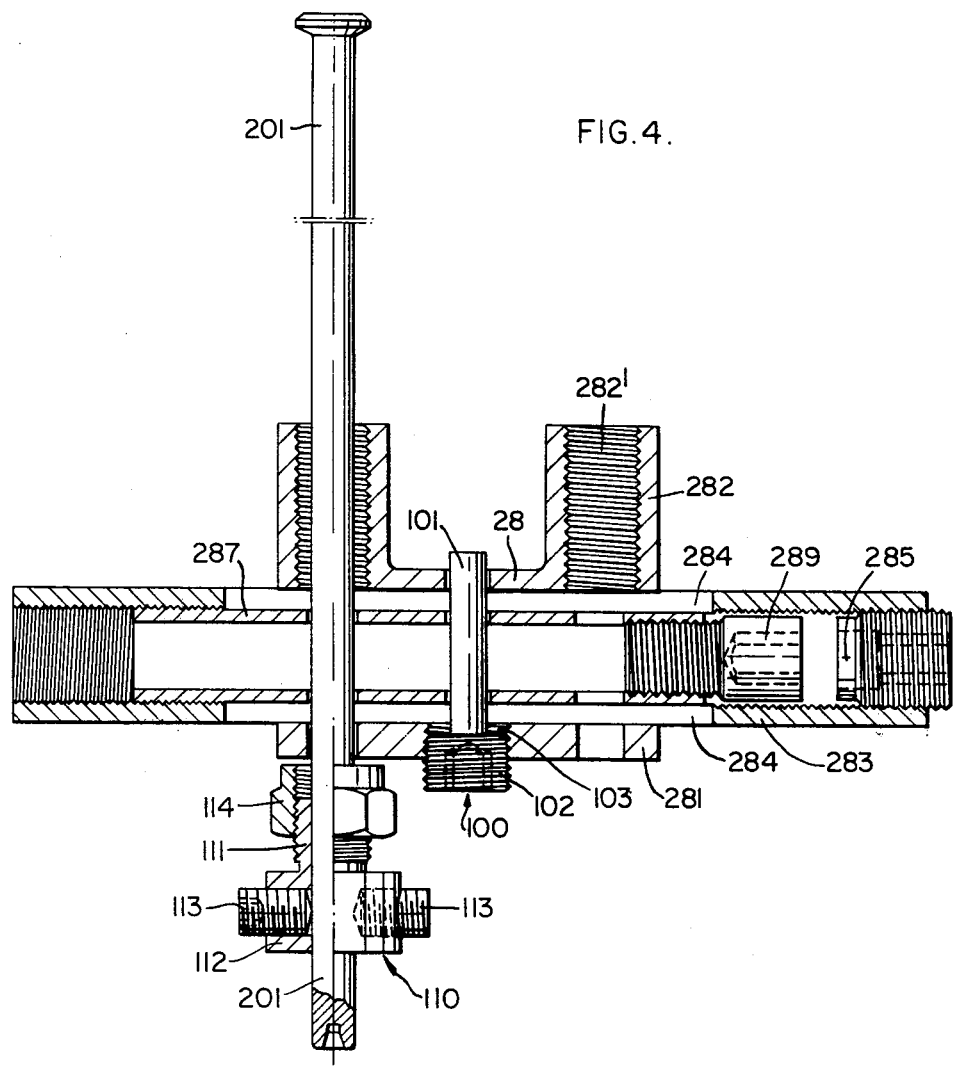

DEVICE FOR EXTERNALLY EXERTING A HOLDING ACTION ON BONE TISSUES

This invention relates to a device for externally exerting a holding action on bone tissues and, more specifically, it relates to a device exerting a holding action on bone tissues in order to achieve external fixation and generally to apply forces in any direction on skeleton segments or a portion thereof, such a device being able to be adjusted at any time to balance possible slacks caused by variations of the elastic reaction of the bone.

It is known that in some cases of fractures of long bones of the limbs, devices are used which externally exert a holding action on the fractured bone fragments in order to keep them in contact with each other.

Such devices presently comprise an outer body provided with two sets of metal pins or nails which come out at right angle from the body. One set of pins is inserted into the bone at one side of the fracture, while the second set is inserted into the bone at the other side of the fracture so that the body remaining outside the limb forms a holding element which keeps the bone segments in contact in order to achieve knitting of the same.

The nails used in the known devices can be either simple through nails passing the bone from one side to the other or threaded nails which are directly screwed on the bone.

Known devices of this type have a drawback in that stability of the holding action thereof depends on the constant elastic reaction of the bone tissue depending in turn on the absence of resorption phenomena. This means that stability of connection between metal members and bone tissue is achieved only in optimal conditions, that is in the absolute absence of complications. These optimal conditions may not occur and especially in particularly complex cases, such as infected fractures and pseudoarthrosis. But also independently of preceding infections, the holding device can act as an infection carrier and this is a drawback of external fixation. In this case the external fixer will not be as reliable as it should be.

Moreover, the stability of connection presently required in osteosynthesis and also necessary to avoid or at least reduce bone resorption phenomena is not achieveable by means of known holding devices.

This invention therefore is intended to eliminate such drawbacks providing a device exerting a holding action on the bone and meeting the following requirements:

obtaining higher stability by actively exerting a known and controllable pressure on the bone tissue on which the metal element exerts the holding action, so that possibility of movements in any direction is avoided;

adjusting the force which the holding element exerts on the bone tissue at any time and also after application, in order to eliminate possible slacks;

avoiding or reducing bone resorption and minimizing risks and consequences of infection;

accordingly, maintaining constant stability of connection.

This invention generally comprises a new type of device for gripping the bone, cooperating with elements adapted to be adjusted as to their position and/or the exerted force related to the bone and with supporting elements adapted to assure a correct and firm position of one or more gripping members in relation to the part to be held and other external elements connecting the fragments of a fracture therebetween.

In order to achieve the essential object of the invention, that is to allow stability of connection to be recovered in the case of possible variations of the elastic strength of the bone, the invention comprises adjustment elements to register the force which the gripping members keep on the bone, as desired and at any time. This is an essential fact meeting the biological needs making it important that stability of connection, e.g. in a fixation, is assured both from starting and then constantly maintained, since this is the only mechanical solution capable of efficiently preventing or at least reducing bone resorption.

To this purpose, the device according to the invention is characterized in that it comprises, in combination and cooperating relationship, mechanical elements in contact with the bone, such elements being provided with gripping members to exert a holding action on the bone; mechanical elements adapted to assure the adjustment of the holding action on the bone; and, supporting elements adapted to assure a correct position of the elements in contact with the bone and of the holding elements.

The invention will be now described in detail in respect to some possible embodiments thereof, which are intended to be illustrative and not restrictive examples of the objects and scope of the invention, which embodiments will be illustrated in the annexed drawings, wherein:

FIG. 1 is a transverse elevation of a first embodiment of the invention;

FIG. 2 is a transverse elevation of a second embodiment of the invention;

FIG. 4 is an axial section of an improved embodiment.

Figure 3:
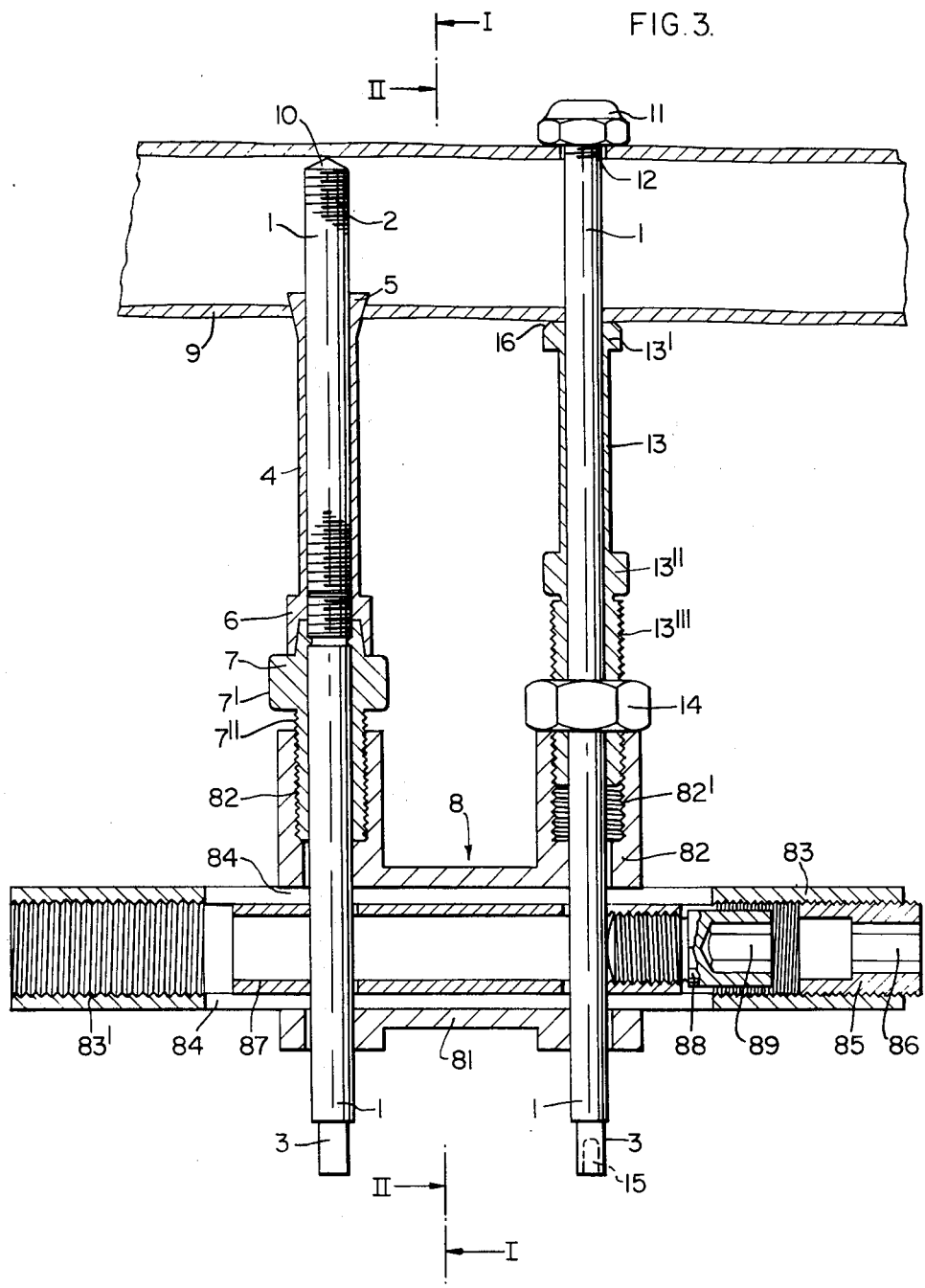
FIG. 3 is a longitudinal sectional view of both embodiments set forth.

With reference to FIG. 1, a first embodiment of the invention, which is useful where it is necessary and/or advisable to act on one side only of the bone, comprises a long central nail 1 provided with a thread 2 along approximately a half length thereof and having a polygonal section spigot 3 mounted at one end thereof.

A small cylindrical tube 4 or sleeve is screwed on threaded portion of the nail, tube 4 being provided with a number of longitudinal slots 5 at one end and with a polygonal enlargement 6 or other similar gripping members at the opposite end. A member 7 can be placed, in engagement relationship, against polygonal enlargement 6, member 7 being provided with an upper polygonal enlarged portion 7' and a cylindrical threaded portion 7" which is screwed in a portion of the above mentioned supporting element 8.

In using this first embodiment, only one hole is drilled in the bone of the same diameter as tube 4 which is inserted in the hole until slots 5 are well inside the bone. Threaded portion 2 of central nail 1 is then inserted in tube 4 and screwed until the end thereof engages the internal face of the opposite wall of the bone. During this operation, threaded portion 2 causes an elastic enlargement of the slotted portion of tube 4, as shown.

While nail 1 is being screwed, small tube 4 is prevented from rotating by exerting a holding action on enlarged end 6 thereof; while going on screwing nail 1 and preventing tube 4 from rotating, the latter is pulled back to the point where the slotted and enlarged portion thereof is fixed, as shown, in the hole drilled in bone 9.

Member 7 first and then supporting element 8 are now inserted on nail 1; portion 7″ of member 7 is screwed on element 8 which is secured on nail 1 in a manner described hereinafter; finally, acting on polygonal enlarged portion 7′, member 7 is drawn into engagement with portion 6 of tube 4 and forced against the same to form a firm clamping of the device.

Once the device is assembled, should any slack occur, e.g. between tube 4 and the bone, suitably acting on end 3 of nail 1 or on portion 7′ of member 7 will be sufficient to restore perfect firmness of the gripping device.

FIG. 2 shows a different embodiment of the invention. In this case nail 1 is provided at one end with an abutment and stop member 11 which can be either integral with nail 1 or removable, in which case the nail is provided with a short thread 12 at this end. Nail 1 is provided with polygonal spigot 3 at the end opposite member 11.

A small tube 13 coaxially slides around nail 1, tube 13 being provided with a suitable enlargement 13′ at one end end a thread 13‴ with a polygonal enlargement 13″ mounted thereon at the opposite end. Threaded portion 13‴ is screwed into a free nut 14 and supporting element 8.

In use, two aligned holes are drilled in bone 9 and nail 1 is inserted therein. Should member 11 be removable, the nail is inserted from below, in respect to the Figure, at threaded portion 12 which is drawn off the bone and on which member 11 is then screwed. Should on the contrary member 11 be fixed, a thin guiding member (not shown) is first inserted into the holes, the guiding member being drawn out and engaged in a blind hole 15 drilled on spigot 3. The guiding member is then withdrawn pulling nail 1 which in this case is inserted from above, in respect to the Figure.

In both cases, once nail 1 has been introduced through the corticals of bone 9, member 11 is drawn into engagement with one of the bone portions; at the opposite side small tube 13, already having nut 14 on its threaded portion 13‴, and element 8 are sequentially inserted on nail 1. Portion 13‴ is completely screwed in element 8 which is then suitably secured on nail 1. Finally, portion 13‴ is unscrewed to the point where portion 13′ of small tube 13 is engaged with the external wall of bone 9, as illustrated. At this point nut 14 is tightened against element 8, thus realizing a firm clamping of the gripping device.

Should any slack occur, it can be eliminated by suitably acting both on portion 13″ of small tube 13 and on spigot 3 of nail 1.

FIG. 3 shows the above mentioned embodiments, such mounted and in transversal sectional view in order to illustrate the structure and functions of supporting element 8.

In this figure the parts already shown in the preceding Figures are referred to with the same references.

The supporting element, generally referred to with reference 8, comprises a number of generally tubular and coaxial members.

A first member includes a tubular body 81, having at least an extending portion 82 provided with a threaded hole 82′, at right angle to the axis of tubular body 81. A second tubular body 83 slides inside body 81, second body 83 being provided with long slots 84 at two diametrically opposite generating lines thereof. Body 83 is provided at one end with a threaded portion in which a threaded nut 85 is received, provided with an axial polygonal-shaped through hole 86. A third tubular body 87 is mounted inside body 83, body 87 being provided with pairs of holes diametrically aligned on both walls thereof. Body 87 as well is provided at one end with an inner thread, wherein a threaded nut 88 is received, provided with an axial blind hole 89.

Tubular bodies 81, 82 and 83 are engaged with each other and they are axially movable in respect to each other; moreover, the threaded portions of bodies 83 and 87 are both mounted on the same side of the device, so that nuts 85 and 88 and relative control holes 86 and 89 are coaxially aligned on the same side of the device.

In use, once the members have been assembled as described with reference to FIGS. 1 and 2, and once nails 1 and small tubes 4 and/or 13 have been suitably inserted in element 8 through threaded hole 82′ and slots 84, and the holes have been drilled on body 87, a wrench, e.g. of the Allen type, is introduced through hole 86 of nut 85 until it engages with hole 89 of nut 88 which is then moved forward to the point where it rests on nail 1. In this way member 87 is moved to the right in the Figure, so that nails 1 are clamped between the walls of the holes drilled on members 87 and 81.

Nut 85 is used to produce, where necessary, the relative movement of bodies 83 and 81 along the same length as that of slot 84 on body 83. In order to stop this movement or to produce a movement in the opposite direction, a second nut can be provided, similar to nut 85, screwed in a thread threaded in opposite end 83′ of member 83.

In FIG. 4, showing a sectional view of a modified device and similar to FIG. 3, so that when possible the various common parts have been indicated with the same references increased by 200, some improvements to the device of the invention are illustrated.

A first improvement consists in using an abutment and stop screw 100 provided with a shank 101 and a head 102, enlarged in respect to the shank and threaded, which screw is inserted into a threaded hole 103, drilled in a wall of body 281, and passes through bodies 287, 283 and 281. Head 102, abutting on the edges of slot 284 of body 283, clamps support body 281 to body 283, thus preventing both axial and rotational movement of support body 281 along and around body 283.

A further improvement is that hole 282′ in protrusion 282 is extended for the whole length of protrusion 282 to the internal wall of the axial hole drilled in body 281; this not only makes construction of the device easier, but allows also a longer movement in small tube 213. Still another improvement is that a further device is used to adjust the position of nail 201. Such a device comprises a body 110 provided with a threaded shank 111 and a cylindrical head 112 integral with shank 111 and provided on the arcuate portion of at least two faces parallel to each other and adapted to allow the engagement of head 112 with a screw spanner. Both shank 111 and head 112 are axially drilled to receive nail 201. Head 112 is also provided with two diametrically opposed threaded holes, each hole receiving an Allen screw 113 adapted to tighten nail 201. A nut 114 is screwed on shank 111. In use, where it is necessary to adjust the position of nail 201, it will be enough to insert body 110, provided with nut 114, on nail 201 until nut 114 is engaged with body 281. Nail 201 is made integral with body 110 by tightening Allen screw 113. At this point, by screwing head 112 on nut 114 it is possible to produce respectively a longer or shorter protrusion of nail 201 from supporting element 28, thus allowing adjustment of the axial force exerted on the bone fragment through nail 201 applied thereto.

As it will be clear, all the forces which can be applied through the movements of the herein described sleeves and nails make it possible what follows:

to draw the portion of fragments adjacent the fracture closer to the device and to move away the opposite portion thereof, while exerting an axial pressure along body 283. This compensates the unbalance of the pressures exerted along body 283.

While the invention has been described with reference to only some of the possible embodiments thereof, it will be clear that it can suggest other possible embodiments to those skilled in the art, without departing, however, from the scope of the invention.

Possible slacks, for example, can be adjusted by putting compressed elastic members, e.g. a spring, between the movable members of the device.

It is also possible that the nail illustrated in FIG. 2 is through in respect to the limb and in this case member 11 is replaced by a member similar to member 13 so that the device on the whole, comprising elements 14 and 8, is in a position symmetrical to the bone.

I claim:

1. A device for externally exerting a holding action on bone tissues comprising:
   (a) first mechanical means adapted to engage the bone and extend at least partially therethrough,
   (b) said first mechanical means including nails provided with axially slidable members thereon for exerting a holding action on the bone;
   (c) second mechanical means for providing adjustment of the holding action in a direction transverse to the bone;
   (d) third mechanical means for adjustably clamping said first and second mechanical means in a selected position; and
   (e) fourth means for axially adjusting at least one of said nails relative to said third mechanical means.

2. A device according to claim 1, characterized in that said third means adapted to clamp said first and second means in the selected position comprise a number of coaxial tubular members, a first external member including a hollow body having at least one external protrusion provided with a threaded hole at right angle to the axis of said hollow body; a second tubular hollow member being engaged inside the cavity of said first member in sliding relationship therewith and being provided with slot-shaped through holes along two diametrically opposed generating lines thereof and with internal threads at both ends thereof; a third tubular hollow member being engaged inside the cavity of said second member in sliding relationship therewith and being provided with at least two diametrically aligned holes on the walls thereof and an internal thread at one end thereof.

3. A device according to claim 2, characterized in that said second and third tubular hollow members have axially sliding threaded nuts inserted at the respective threaded ends thereof.

4. A device for externally exerting a holding action on bone tissues comprising:
   (a) first mechanical means adapted to engage the bone and extend at least partially therethrough,
   (b) said first mechanical means including nails provided with axially slidable members thereon for exerting a holding action on the bone;
   (c) second mechanical means for providing adjustment of the holding action in a direction transverse to the bone;
   (d) third mechanical means for adjustably clamping said first and second mechanical means in a selected position;
   (e) said nails being provided with a thread extended for approximately half the length thereof, while the end opposite the thread is provided with a polygonal spigot; said threaded half of said nail being engaged in axially sliding relationship with a threaded sleeve or tube provided with a number of slots at one end and members adapted to grip the sleeve at the opposite end; said sleeve also engaging said second mechanical means which includes pressure means engaged with said third mechanical means.

5. A device according to claim 4, characterized in that said pressure means comprises threaded portions engaged in axially sliding relationship with threaded holes drilled in said third mechanical means.

6. A device according to claim 4, wherein said second mechanical means adapted to assure the adjustment of said members exerting a holding action on the bone fragments comprise a body provided with a threaded shank and a cylindrical head enlarged in respect to the shank, said body being provided with an axial hole through said shank and said head for receiving said holding members; said second mechanical means comprise also a nut which can be screwed on said shank, said nut abutting on the surface of the third means, said cylindrical head being provided with two holes on the arcuated surface thereof, each hole receiving an Allen screw adapted to make said holding member integral with said cylindrical head.

7. A device according to claim 6, wherein said third means adapted to clamp said second means and said members, exerting a holding action on the bone, in the selected position comprise also an abutment and stop screw provided with a shank and an enlarged and threaded head, said head being inserted into a threaded hole drilled in a portion of the third means and abutting on the edges of a slot.

8. A device for externally exerting a holding action on bone tissues comprising:
   (a) first mechanical means adapted to engage the bone and extend at least partially therethrough,
   (b) said first mechanical means including nails provided with axially slidable members thereon for exerting a holding action on the bone;
   (c) second mechanical means for providing adjustment of the holding action in a direction transverse to the bone;
   (d) third mechanical means for adjustably clamping said first and second mechanical means in a selected position;
   (e) said nails being provided at one end with members adapted to abut on said bone and are inserted in axially sliding relationship into an internally smooth sleeve; said second mechanical means comprising pressure means engaged with said third mechanical means are engaged with the sleeve end farthest from said bone; the end of said nails is provided with a polygonal spigot having also an axial blind hold thereon.

9. A device according to claim 8, characterized in that said pressure means comprises threaded portions engaged in axially sliding relationship with threaded holes drilled in said third mechanical means.

10. A device according to claim 8 characterized in that said members adapted to abut said bone are self-locking threaded nuts.

11. A device according to claim 8 characterized in that said members adapted to abut said bone are disc-shaped enlargements of the nail end.

12. A device according to claim 8 characterized in that said members adapted to abut said bone are inverted frusto-conical shapes.

* * * * *